(12) United States Patent
Gramnäs

(10) Patent No.: US 6,855,170 B2
(45) Date of Patent: Feb. 15, 2005

(54) DEVICE IN A LEG PROSTHESIS

(75) Inventor: Finn Gramnäs, Kinna (SE)

(73) Assignee: Gramtec Innovation AB, Kinna (SE)

( * ) Notice: Subject to any disclaimer, the term of this patent is extended or adjusted under 35 U.S.C. 154(b) by 2 days.

(21) Appl. No.: 10/362,300

(22) PCT Filed: Aug. 22, 2001

(86) PCT No.: PCT/SE01/01783

§ 371 (c)(1),
(2), (4) Date: May 13, 2003

(87) PCT Pub. No.: WO02/15826

PCT Pub. Date: Feb. 28, 2002

(65) Prior Publication Data

US 2004/0044417 A1 Mar. 4, 2004

(30) Foreign Application Priority Data

Aug. 25, 2000 (SE) .............................................. 0003039

(51) Int. Cl.$^7$ ................................................. A61F 2/66
(52) U.S. Cl. ....................................................... 623/49
(58) Field of Search .............................. 623/49, 47, 48

(56) References Cited

U.S. PATENT DOCUMENTS

| | | | |
|---|---|---|---|
| 1,289,580 A | * 12/1918 | Vincenti | ...................... 623/52 |
| 2,470,480 A | 5/1949 | Fogg | |
| 2,749,557 A | 6/1956 | Riddle | |
| 3,754,286 A | 8/1973 | Ryan | |
| 3,851,337 A | 12/1974 | Prahl | |
| 3,871,032 A | * 3/1975 | Karas | ........................... 623/26 |
| 4,499,613 A | 2/1985 | Yarrow | |
| 5,139,525 A | * 8/1992 | Kristinsson | ................... 623/55 |
| 5,258,038 A | * 11/1993 | Robinson et al. | .............. 623/49 |
| 5,957,981 A | * 9/1999 | Gramnas | ...................... 623/47 |
| 6,187,052 B1 | * 2/2001 | Molino et al. | ................. 623/52 |

FOREIGN PATENT DOCUMENTS

| | | |
|---|---|---|
| DE | 818828 | 10/1951 |
| DE | 838480 | 5/1952 |
| FR | 800547 | 7/1936 |
| SE | 456134 B | 9/1988 |
| SE | 469780 B | 9/1993 |
| SE | 511750 C2 | 8/1996 |
| WO | WO 88/06431 A1 | 9/1988 |
| WO | WO 91/15171 A1 | 10/1991 |
| WO | WO 96/25898 A1 | 8/1996 |
| WO | WO 00/76429 A1 | 12/2000 |

OTHER PUBLICATIONS

International Search Report mailed from the Swedish Patent Office on Nov. 27, 2001.
International Preliminary Examination Report completed by the Swedish Patent Office on Jul. 17, 2002.

* cited by examiner

*Primary Examiner*—Bruce E. Snow
(74) *Attorney, Agent, or Firm*—Gardner Carton & Douglas LLP

(57) ABSTRACT

A device in a leg prosthesis which via a pivot axle is connected to the leg prosthesis, wherein first means are arranged to permit a limited rotation of the foot with respect to the leg prosthesis from an initial position, in which the leg prosthesis and the foot have a certain angle with respect to each other and second means are arranged to permit a stepless adjustment of the angle between the prosthesis and the foot in the initial position.

10 Claims, 3 Drawing Sheets

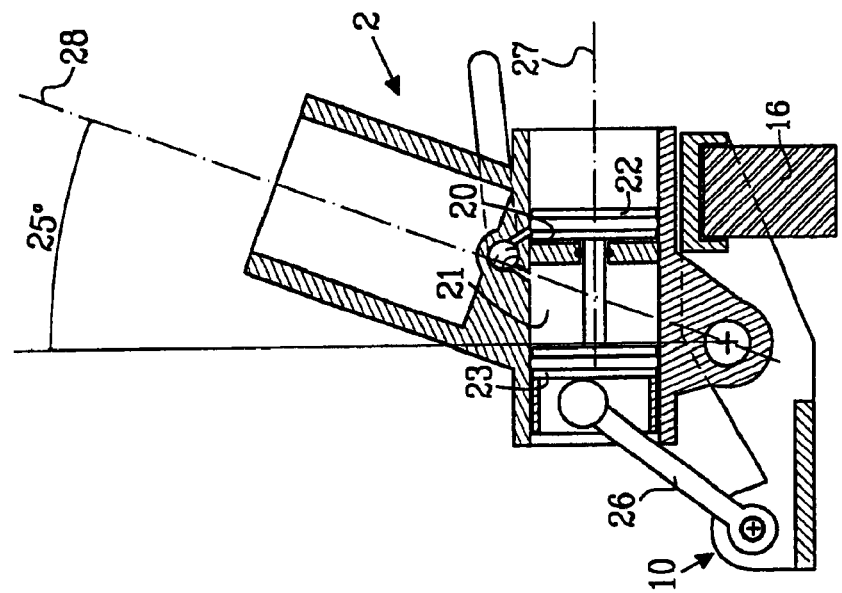
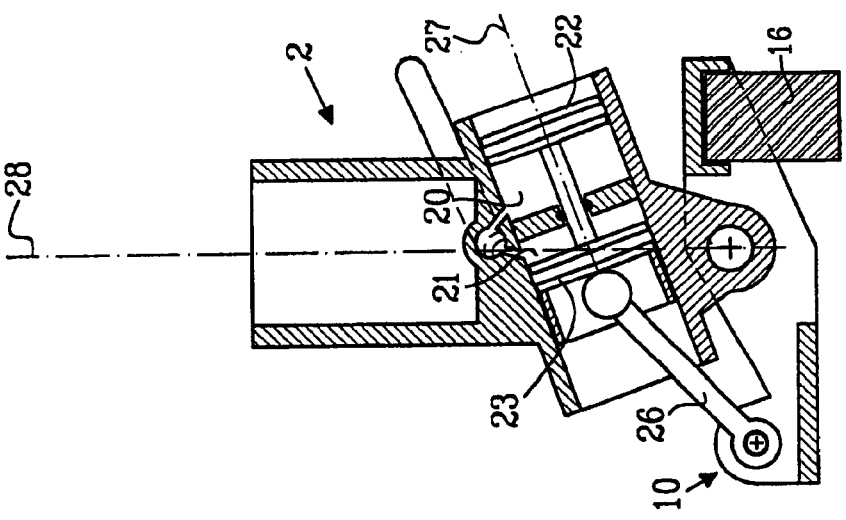
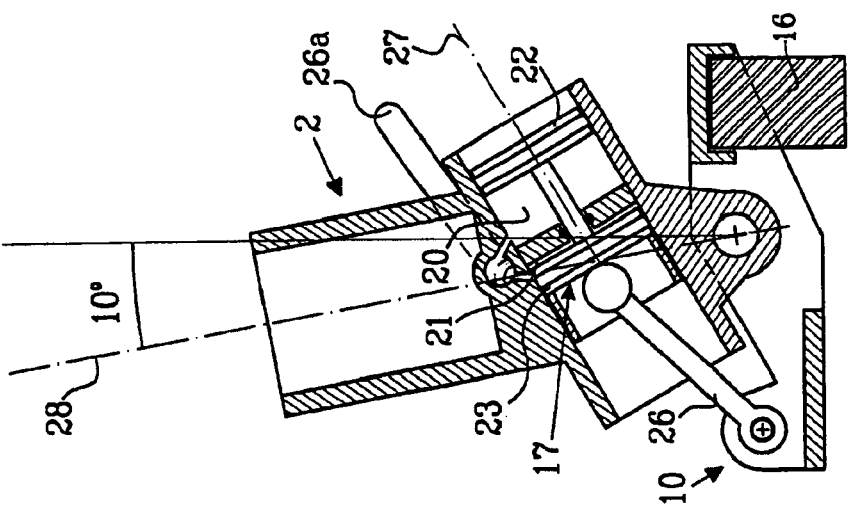

DEVICE IN A LEG PROSTHESIS

TECHNICAL FIELD

The present invention refers to a device in a leg prosthesis according to the preamble of claim 1. The invention especially refers to a device in a leg prosthesis provided with a foot which via a pivot axle is connected to the leg prosthesis and wherein the angular position between the foot and the leg prosthesis is adjustable to a desired angular position.

BACKGROUND OF THE INVENTION

It is well-known among prosthesis wearers that walking in downhill slopes is problematic. If the prosthesis wearer does not have the possibility to adjust the foot angle only the heel will contact the ground when walking in a steep downhill. If the foot angle exceeds a certain degree it will due to the absence of certain muscle groups be difficult to resist the knee from collapsing. Therefor the prosthesis wearer often chooses to walk sideways downhill.

Prosthesis wearers that do not have a height adjustable foot have problems changing to a shoe with another heel height, and to quickly choose to walk without shoes. Individual adaption of the foot in height also reduces the problem of back pain and worn out hip-joints.

In order to reduce the above problem prostheses with adjustable angular position between the foot and the leg prosthesis have been developed. It is for example known through SE 511 750 a device in a leg prosthesis provided with a foot which via a pivot axle is connected to a leg prosthesis and in which the angular position between the leg prosthesis and the foot is adjustable. For increasing the usefulness for prostheses for users whose amputation site is located just above the foot it is necessary that the prosthesis including adjustment mechanisms have a compact design. In SE 511 750 this is provided by designing the adjustment mechanism in the form of a curved cylinder and curved piston parts located therein. The complicated geometry make this type of prosthesis expensive and complicated to manufacture.

BRIEF DESCRIPTION OF THE INVENTION

An object of the invention is to provide a device in a leg prosthesis provided with a foot which via a pivot axle is connected to the leg prosthesis and wherein the angular position between the foot and the leg prosthesis is adjustable to a desired angular position and which admits a compact installation of the adjustment mechanisms of the prosthesis. A further object of the invention is to provide a device in a leg prosthesis with adjustable angular position between the foot and the leg prosthesis which admits utilization of adjustment mechanisms with simple geometries at which the manufacturing cost can be reduced.

These objects have been achieved by a device in a leg prosthesis according to the characterizing part of claim 1. By providing the device with a lever arm which is pivotally connected to said leg prosthesis and said foot, wherein said lever arm is arranged to cooperate with on one hand said first member which admits a limited angular adjustment between the lever arm and the foot and on the other hand with said second member which admits an angular adjustment between the lever arm and the leg prosthesis for adjusting the initial position, a compact design of the prosthesis and adjustment mechanisms comprised therein at the same time as the adjustment means can be designed with a simple geometry. The simple geometry is provided by the fact that the angular adjustment between the leg prosthesis and the foot is transmitted through the lever arm.

Preferred embodiments are stated in the dependant claims.

DESCRIPTION OF THE DRAWINGS

One embodiment of the invention will below be described in detail with reference to the attached drawing figures, wherein FIGS. 2a-2c show side views of the invention with different adjustments of the angular position between the leg prosthesis and the lever arm and FIG. 3 shows the prosthesis during loading of the heel.

PREFERRED EMBODIMENT

Figure 1:
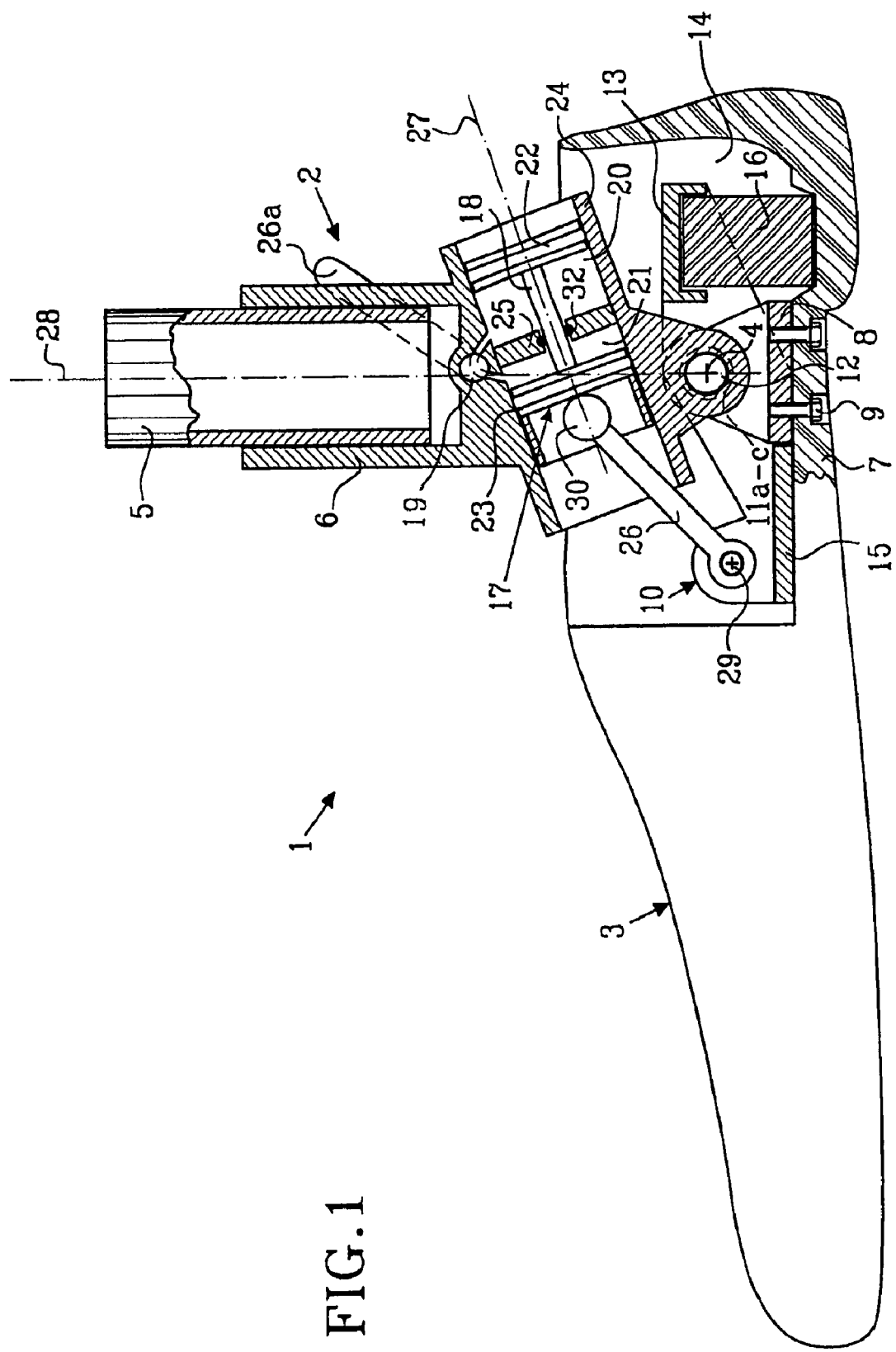
FIG. 1 shows a side view of a prosthesis according to the invention.

In FIG. 1 there is shown a prosthesis generally denoted 1. The prosthesis comprises a leg prosthesis 2 and a foot 3. The leg prosthesis connected to the foot via a pivot axle 4. The leg prosthesis is constructed in a manner well-known to the person skilled in the art, for example with a tubular lower leg portion 5 which is attached in a socket 6, said socket being connected to or comprising said pivot axle 4. The foot 3 is also constructed in a manner well-known to the person skilled in the art and comprises a foot blade 7, preferably provided with a foot-like casing. The foot 3 is preferably provided with an attachment plate 8 which is connected to the pivot axle 4. The attachment plate 8 is anchored to the foot in any manner well-known to the person skilled in the art, for example by a screw or rivet joint 9. The foot 3 and the leg prosthesis 2 are via the pivot axle 4 rotatably connected to each other.

The prosthesis 1 further comprises a lever arm 10 which is pivotally connected to the leg prosthesis 2 and to the foot 3. In a preferred embodiment of the invention the lever arm 10 is supported in a shaft which is common with said pivot axle 4. This is provided by a manner well-known to the person skilled in the art, for example by constructing the leg prosthesis 2, the attachment plate 8 of the foot and the lever arm 10 with inlets 11a–c an rotatably connect these by means of a shaft 12. The lever arm 10, which preferably extends substantially parallel to the foot blade 7, is designed with a first end 13 extending from the pivot axle 4 rearwardly to a heel area 14 of the foot 3 and a second part 15 extending from the pivot axle forwards in the foot 3. In a preferred embodiment of the invention the first end 13 is arranged to cooperate with first means 16 adapted to permit a limited rotation of the foot 3 with respect to the leg prosthesis 2 from an initial position and the second end 15 is arranged to cooperate with second means 17 arranged to permit a stepless adjustment of the angle between the prosthesis and the foot in the initial position. This means that the first 16 and second 17 means through their cooperation with the lever arm 10 limit a free rotatability between the leg prosthesis and the foot.

The lever arm 10 is preferably chamferred at the first end 13 on the lower side facing the foot blade, at which the lever arm can be rotated clockwise according to the figure without bumping against the foot blade. In the same way the opposite end 15 of the lever arm 10 is recessed so that the lever arm can be rotated clockwise in the figure without bump against the second means 17. In this way the lever arm is preferably designed with a substantially rhomb-shaped cross section with possible projecting parts in which the lever arm is provided with a pivot axle 29. In a preferred embodiment the prosthesis 1 is constructed with a double set of lever arms arranged on opposite sides of the symmetry axis of the lower leg tube 5. The first end 13 of the lever arm is at its upper end facing towards the lower leg tube 5 provided with means permitting cooperation with the resilient element 16. In case one lever arm 10 is utilized this means may comprise a projection portion extending vertically and inwardly in the figure, and contacts the upper surface of the resilent element 16. In case two lever arms are utilized this projection may connect both lever arms.

In preferred embodiments of the invention the second means 17 are arranged to take a first condition in which rotation between the lever arm 10 and the leg prosthesis 2 is permitted and a second condition in which an unrotatable connection is created between the lever arm 10 and the leg prosthesis 2. This is preferably provided by the fact that the second means 17 comprises an element 18 which is displaceable with respect to the leg prosthesis and members 19, 20, 21 for keeping the displaceable element in a desired displacement position. In a preferred embodiment the displaceable element 18 consists of a piston 18 with outwardly projecting ring flanges 22, 23 and which is displaceable in a cylinder 24 attached to the leg prosthesis 2. The members 19, 20, 21 for the piston in a desired displaced position with respect to the cylinder 24 further comprise a ring wall 25 in the cylinder, said ring wall dividing the space between the ring flanges of the piston into two chambers 20, 21 and a two-way valve 19 which in open position permits flow of medium between the chambers 20, 21 and in closed position prevents such flow of medium The two-way valve 19 is in a known manner adjustable between its first and second position by a control stick 26a from the outside of the prosthesis. The two-way valve preferably comprises a rotatable cylindric valve body with two openings, which in the open position of the valve are facing and communicate with a respective chamber 20, 21 via holes in the cylinder wall. The two ring flanges are supported by a longitudinal axle 31 extending through an inlet in the ring wall 25. The inlet is preferably sealed by a sealing ring 32 preventing overflow of hydraulic fluid through the inlet in the ring wall 25. The cylinder 24 and the piston 18 are provided in the leg prosthesis above the pivot axle 4.

In order to permit a compact construction of the prosthesis 1 and adjustment mechanisms contained in the prosthesis 1 such as the above mentioned second means 17 the cylinder is preferably arranged with a symmetry axis 27 making an angle with a longitudinal axis 28 of the leg prosthesis in the direction of the leg. Preferably the symmetry axis 27 crosses the foot blade 7 or close to a toe region of the foot blade 7 when the leg prosthesis 2 is in an upright position. In a preferred embodiment the symmetry axle 27 is arranged substantially in parallel to the lever arm 10 when the leg prosthesis has taken an angular position in which the leg prosthesis is rotated maximally backwards towards the heel area 14 of the foot This position of the lever arm 10, leg prosthesis and second means 17 is shown in FIG. 2c. Through this design a very compact construction of the prosthesis is achieved. In a preferred embodiment of the invention the maximum backward rotation of the leg prosthesis 2 with respect to the foot 3 is 25°. In this case the angle between the symmetry axle 27 and longitudinal axis 28 is 65°.

In a preferred embodiment of the invention the second end 15 of the lever arm 10 is connected to said second means by way of a link 26 pivotally supported in both ends. The link 26 is pivotally supported in both ends by first and second pivot axles 29, 30 wherein the first pivot axle 29 preferably is arranged on the second end of the lever arm and the second pivot axle 30 is arranged in an extension of the piston 18. The lengths of the lever arm 10 and the link 26 are so adapted that the leg prosthesis 2 can be brought from a first extreme position in which the leg prosthesis is angled maximally forwards, which in one embodiment amounts to about 10° forwards from a vertical position, this position being shown in FIG. 2a, to a second extreme position in which the leg prosthesis is angled maximally backwards, which in one embodiment amounts to about 25° backwards from a vertical position, this adjustment being shown in FIG. 2c, without the piston 18 being locked in the cylinder 24 or the link 26 being locked against the cylinder 24.

The first means 16 arranged to permit a limited rotation of the foot 3 with respect to the leg prosthesis 2 from an initial position, in which the leg prosthesis and the foot have a certain angle with respect to each other, in one preferred embodiment comprises a flexible body, preferably a resilient element of for example rubber. The resilient element 16 is mounted in connection to the first end 13 of the lever arm 10, which extends from said pivot axle backwards towards a heel area 4 of the foot 3. In on embodiment of the invention the resilient element is provided with means permitting an adjustment of the flexibility of the resilient element. These means can be designed as a screw which prestresses the resilient element to a desired stiffness.

In FIG. 2a there is shown the adjustment mechanism for adjustment of the angular position between the lever arm 10 and the leg prosthesis 2 in a maximally forward inclined position which in one embodiment constitutes 10°.

FIG. 2b the adjustment mechanism for adjusting the angular position between the lever arm 10 and the leg prosthesis 2 is shown in upright potion.

In FIG. 2c there is shown the adjustment mechanism for adjusting the angular position between the lever arm 10 and the leg prosthesis 2 in a maximally backwardly inclined position which in one embodiment constitutes 25°.

Other details in the FIGS. 2a–2c are common with FIG. 1 and will therefor not be described in detail.

Figure 3:
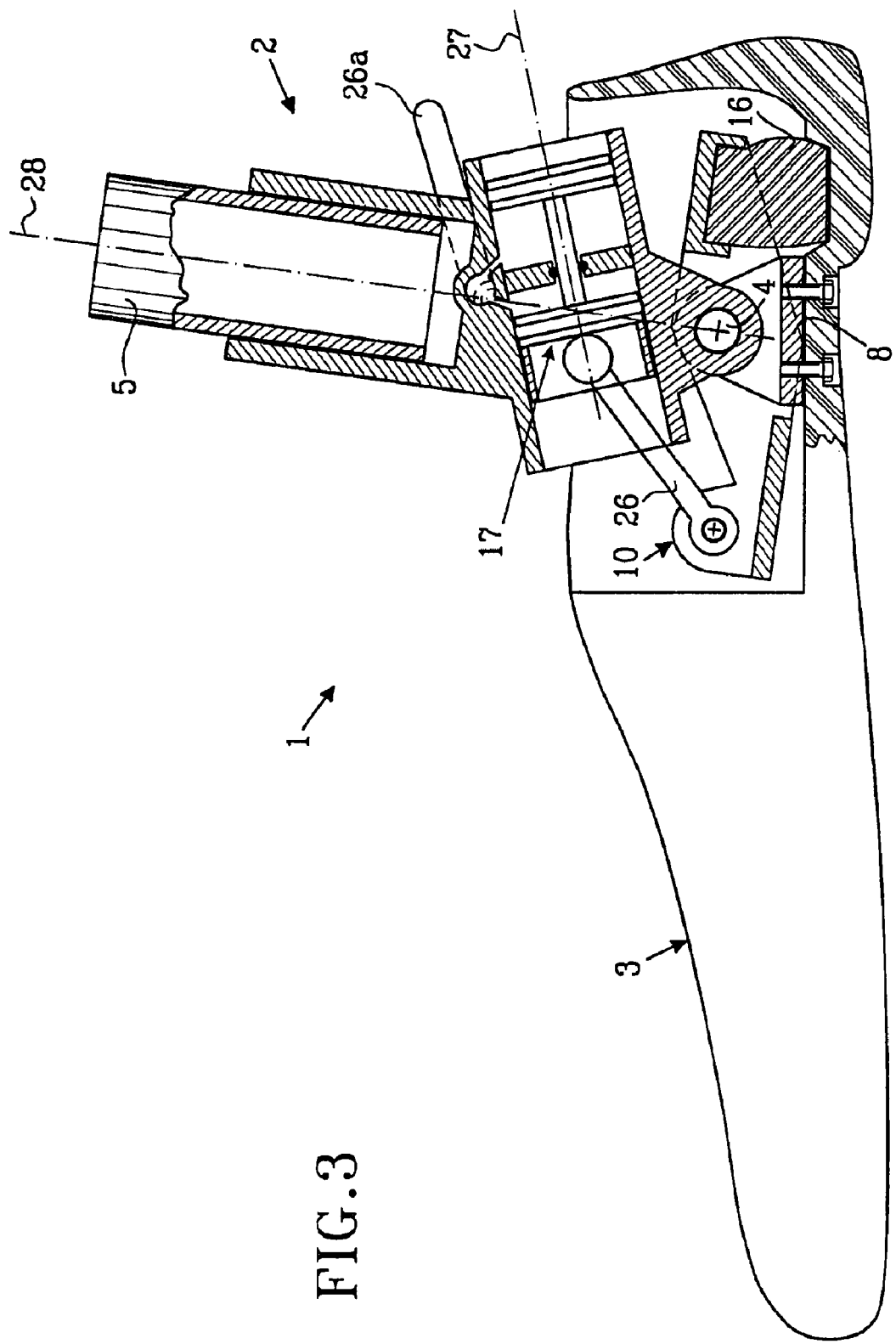

In FIG. 3 the prosthesis is shown under load of the heel at walk. At heel strike at walk the rubber element 16 will be compressed. When moving the weight to the leg striking the ground the upward force acting on the heel will create a moment indicated by arrows in FIG. 3, which against the action of the spring force in the resilient element will rotate the foot downwards until the foot blade will be in contact with the ground. The resilient element 16 herewith acts as a shock absorber which absorbs the force that occurs at heel strike. Other details are common with FIG. 1 and are therefor not described, however the two-way valve is shown in a closed position in which the channel between the two chambers 20, 21 are closed and the two openings of the valve are located in a closed position and are facing away from the above mentioned holes in the cylinder wall.

An unloaded foot will take a set initial position since the resilient member strives at taking its expanded position.

In case one would like to change the initial position of the angle between the leg prosthesis and the link arm and by that the initial position between the foot and the leg prosthesis the two-way valve 19 is opened at which an overflow of hydraulic medium can take place between the chambers 20, 21. This involves that the piston 18 can be displaced in a stepless way with respect to the cylinder 24 at which the angular position between the leg prosthesis 2 and the lever arm 10 is changed. When the desired angular position has been obtained the valve is closed at which the lever arm 10 and the leg prosthesis 2 are unrotatably connected with respect to each other.

The invention is not limited to the above described embodiments but can be varied within the scope of the claims.

What is claimed is:

1. A device in a leg prosthesis provided with a foot which via a pivot axle is connected to the leg prosthesis, wherein a first means is provided to permit a limited rotation of the foot with respect to the leg prosthesis from an initial position, in which the leg prosthesis and the foot has a certain angle relative to each other and a second means is arranged to permit a stepless adjustment of the angle between the prosthesis and the foot in the initial position, characterized in that the device comprises a lever arm which is pivotally supported with respect to said leg prosthesis and said foot and that said lever arm is arranged to cooperate with on one hand said first means at which a limited angular adjustment between the lever arm and the foot is permitted under cooperation with said first means, and on the other hand with said second means at which an angular adjustment between the lever arm and the leg prosthesis is permitted while adjusting said initial position and wherein said second means is arranged to take a first position in which rotation between the lever arm and the leg prosthesis is permitted and a second position in which an unrotatable connection between the lever arm and the leg prosthesis is provided.

2. The device as claimed in claim 1, characterized in that the second means comprises an element which is displaceable with respect to the leg prosthesis and members for keeping the displaceable element in a desired displacement position.

3. The device as claimed in claim 2, characterized in that the displaceable element comprises a piston with outwardly projecting ring flanges, which is displaceable in a cylinder attached to the leg prosthesis, and that the members for keeping the piston in a desired displacement position with respect to the cylinder comprise a ring wall in the cylinder dividing the space between the ring flanges of the piston into two chambers and a two-way valve which in open position permits flow of medium between the chambers and in closed position prevents such flow.

4. The device according to claim 3, characterized in that said cylinder has a symmetry axis making an angle with a longitudinal axis of the leg prosthesis.

5. The device according to claim 4, characterized in that said second means permits an adjustment of said initial position between a first angular position in which the leg prosthesis is rotated maximally forwards towards a toe portion of said foot and a second angular position in which the leg prosthesis is rotated maximally backwards towards a heel portion of said foot.

6. The device according to claim 5, characterized in that said symmetry axis is arranged substantially in parallel with said lever arm when the leg prosthesis has taken its second angular position.

7. The device according to claim 1, characterized in that said lever arm is supported in an axle which is common with said pivot axle connecting the foot to the leg prosthesis.

8. The device according to claim 1, characterized in that said lever arm has a first end extending from said pivot axle backwards towards a heel area of the foot and a second end extending from said pivot axle forwards towards the front area of the foot, that said first end is arranged to cooperate with said first means and that said second end is arranged to cooperate with said second means.

9. The device according to claim 8, characterized in that said second end is coupled to said second means through a link which is pivotally supported at both of its ends.

10. The device according to claim 8, characterized in that said first means comprises a flexible body arranged between the foot and the first end of the lever arm at which the flexible body is adapted to be compressed upon rotation of the lever arm towards the foot at the first end of the lever arm.

* * * * *